United States Patent [19]

Martin

[11] 4,254,910
[45] Mar. 10, 1981

[54] PACKAGE FOR THE CONTROLLED RELEASE OF VOLATILE SUBSTANCES

[75] Inventor: James P. Martin, Richmond, Va.

[73] Assignee: Reynolds Metals Company, Richmond, Va.

[21] Appl. No.: 83,581

[22] Filed: Oct. 11, 1979

[51] Int. Cl.³ .............................................. A61L 9/04
[52] U.S. Cl. ..................................................... 239/60
[58] Field of Search ...................... 206/0.5, 524.1, 219; 239/53, 54, 55, 56, 57, 60; 156/254, 290, 344; 229/80

[56] References Cited

U.S. PATENT DOCUMENTS

| | | |
|---|---|---|
| 3,145,112 | 8/1964 | Boegershausen . |
| 3,387,978 | 6/1968 | Major . |
| 3,459,117 | 8/1969 | Koch . |
| 3,675,844 | 7/1972 | Sorrell .................................. 229/80 |
| 3,871,518 | 3/1975 | Murray . |
| 3,939,971 | 2/1976 | Tulis . |
| 4,058,425 | 11/1977 | Thrun .................................. 156/291 |
| 4,141,997 | 2/1979 | Syroha . |
| 4,145,001 | 3/1979 | Weyenberg . |

Primary Examiner—Herbert F. Ross
Attorney, Agent, or Firm—Glenn, Lyne, Girard & McDonald

[57] ABSTRACT

A packaging system for the controlled release of volatile substances is disclosed. This packaging system comprises a pair of outer vapor-impermeable barrier layers and a vapor-permeable central layer which is bonded to each of the pair of vapor-impermeable outer layers, with the volatile material being contained between the central vapor-permeable layer and each of the outer vapor-impermeable barrier layers. The central vapor-permeable layer is formed from a pair of vapor-permeable webs which are bonded to one another. The strength of the bond holding the vapor-permeable webs together is less than the strength of the bond between the vapor-permeable central layer and each of the outer vapor-impermeable barrier layers such that upon exerting a separating force on the outer vapor-impermeable barrier layers the central vapor-permeable webs will split, forming a pair of vapor-permeating members.

10 Claims, 4 Drawing Figures

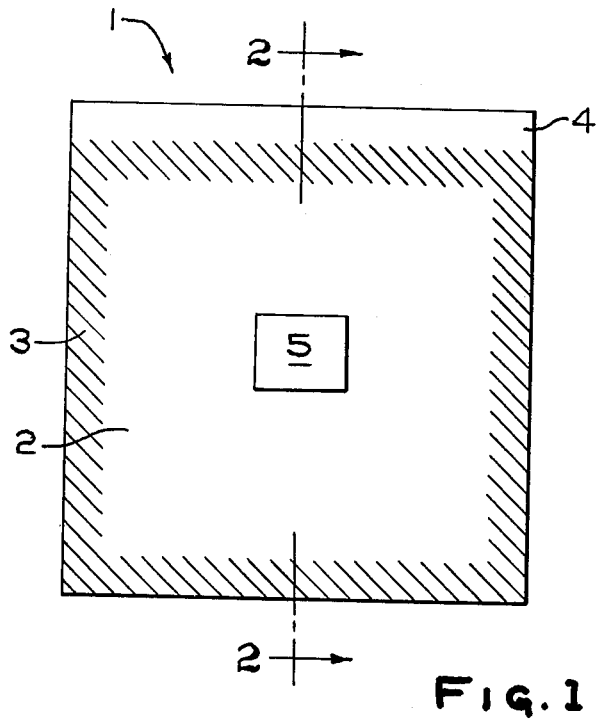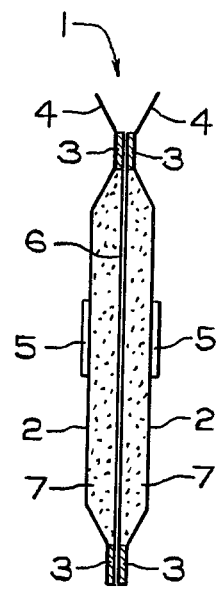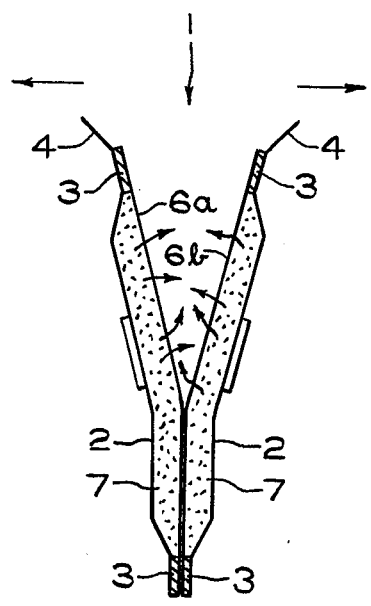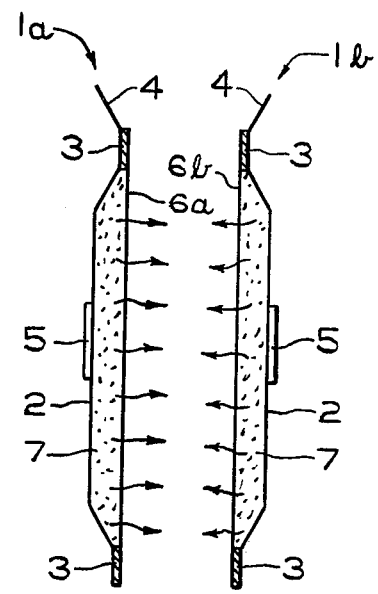

PACKAGE FOR THE CONTROLLED RELEASE OF VOLATILE SUBSTANCES

BACKGROUND OF THE INVENTION

Volatile substances, such as perfumes and deodorizers, are commonly employed as room air fresheners. It is common to contain a liquid including such volatile substances in a glass bottle having a wick. When exposed to the atmosphere, the wick acts to permit the permeable vapors to escape from the bottle and into the atmosphere. Such glass bottles are bulky, breakable and costly.

More recently, volatile air fresheners have been packaged in plastic containers which are of a lighter weight and less costly. However, some of these plastics are subject to attack by either the volatile material or its liquid carrier. It is thus desirable for the volatile material to be held by a solid carrier, such that glass bottles or the like are not required to contain this material, and thus reducing weight and cost for the packaging system.

It is also desirable that the packaging system employed for the controlled release of such volatile materials be as small and convenient for the consumer as possible. Consumers often hide or mask the presence of a room deoderizer. Thus, it is desirable that the packaging system be small and convenient to use so that the deoderizer may be located in out-of-the-way places.

As room deoderizers have become less unsightly and bulky, it is becoming more common for the consumer to use multiple deoderizers throughout the home. It is also desirable, therefore, to provide multiple fresheners in a single package.

THE PRESENT INVENTION

By means of the present invention, a packaging system for the controlled release of volatile substances, and particularly suitable for solid air deoderizers, is disclosed. The packaging system of the present invention comprises a pair of outer vapor-impermeable barrier layers, a central vapor-permeable layer which is bonded to each of the outer vapor-impermeable barrier layers, with the volatile material being positioned between the central vapor-permeable layer and each of the outer vapor-impermeable barrier layers. The central vapor-permeable layer is formed from a pair of vapor-permeable webs which are bonded to one another. The strength of the bond holding the vapor-permeable webs together is less than the bond strength between each of the webs forming the central vapor-permeable layer and their corresponding outer vapor-impermeable barrier layers. Thus, upon exerting a parting force on the outer vapor-impermeable barrier layers, the webs forming the central vapor-permeable layer split, thus forming a pair of members having a vapor-permeable exposed surface to permit the volatile vapors to escape into the atmosphere. The outer vapor-impermeable barrier layers may each be provided with a fastening means to permit the exposed packages each to be located on vertical surfaces, such as a wall or the like.

BRIEF DESCRIPTION OF THE DRAWINGS

The packaging structure of the present invention will be more fully described with reference to the drawings in which:

FIG. 1 is a front elevational view of a packaging system according to the present invention;

FIG. 2 is a cross-sectional view taken along line 2—2 of FIG. 1;

FIG. 3 is a cross-sectional view illustrating the packaging system of the present invention in a partially opened position; and FIG. 4 is a cross-sectional view illustrating the packaging system of the present invention in its fully opened position to form a pair of vapor-permeable members.

DETAILED DESCRIPTION OF THE PREFERRED EMBODIMENTS

Turning to FIGS. 1 and 2, the packaging structure of the present invention is shown. The packaging system 1 includes a pair of outer vapor-impermeable layers 2. The term "vapor-impermeable" as used herein refers to the inability of vapors of the volatile substance being contained by the package 1 to escape through the outer barrier layers 2. A sealed region 3 is illustrated along the edges of the package 1 and an edge or lip region 4 of each of the outer vapor-impermeable barrier layers 2 is illustrated as being unbonded. The purpose of this edge or lip region 4 will be more fully described below. The outer vapor-impermeable barrier layers 2 may each be formed of a single plastics resin layer which is impermeable to the vapors of the volatile substance contained within the package 1, such as high density polyethylene. Preferably, however, the outer vapor-impermeable barrier layers 2 are formed of a laminate comprising a central metal foil barrier lamina, such as aluminum foil, an outer protective plastics resin film lamina, such as a polyester or polyethylene film and an inner plastics resin film lamina, which is preferably formed of a heat-sealable material, such as polyethylene.

As can best be seen in FIG. 2, a central vapor-permeable layer 6 is bonded to each of the outer vapor-impermeable barrier layers 2 at the seal region 3. As used herein, the term "vapor-impermeable" refers to the ability of vapors of the volatile substance being contained by the package 1 to escape through the central layer 6. Preferably, this seal 3 is a heat-seal, formed by positioning the layers forming the packaging structure 1 between a pair of heated dies or bars. While the seals 3 are preferably formed by heat sealing, if desired, these seals could also be formed by adhesive bonding. In forming the packaging structure 1 of the present invention, the side and bottom seals are formed in a first stage, producing a pair of bag-like structures having as a common wall the central vapor-permeable layer 6. The volatile material 7 to be packaged within the packaging structure 1 is then fed between the central vapor-permeable layer 6 and each of the outer vapor-impermeable barrier layers 2 through the top openings, with these openings then being sealed in the same manner as the side and bottom seals were formed.

FIGS. 3 and 4 illustrate the opening of the packaging structure 1 of the present invention to expose the volatile material 7 to the atmosphere. This opening is accomplished by means of a separation of the central vapor-permeable layer 6. Central vapor-permeable layer 6 is formed from a pair of vapor-permeable webs 6a and 6b. These webs 6a and 6b are bonded to one another by adhesive bonding or heat-sealing prior to formation of the packaging structure 1. Preferably, these webs 6a and 6b are bonded to one another by means of adhesive bonding. The webs 6a and 6b are formed of a material which is permeable to volatile vapors, such as cellulose, cotton, rayon, vapor-permeable plastic films and the like. Preferably, the webs 6a and 6b are formed of nonwoven rayon webs.

As the outer vapor-impermeable barrier layers 2 are manually separated from one another, the bonded webs 6a and 6b separate from one another. The bond strength between the webs 6a and 6b themselves is selected to be less than the bond strength between the webs 6a and 6b and their corresponding outer vapor-impermeable layers 2, thus assuring that the bond between the webs 6a and 6b will be broken rather than the seal between the vapor-impermeable barrier layers 2 and the webs 6a or 6b. The vapor-impermeable barrier layers 2 are separated by one another preferably by pulling apart the unbonded lip or edge portion 4 of each of these layers 2. Of course, other separating means may be employed, however, the illustrated opening means 4 is simple and requires no additional components or structure. When the webs 6a and 6b are fully separated, two vapor-permeable structures 1a and 1b result.

The outer vapor-impermeable barrier layers 2 may each include a fastening means 5 attached thereto. These fastening means 5 are preferably adhesive means, such as adhesive dots or tapes, which may each include a protective covering. These adhesive means 5 may be employed to adhere the opened permeable members 1a and 1b to a surface, such as a wall, table or the like.

The volatile material 7 which is contained within the packaging structure 1 is preferably a solid material. This material 7 could be a web which has been saturated with a liquid volatile substance, such as a room deodorizer. However, it is preferred that the volatile material be of a dry nature. Particularly suitable to packaging according to the present invention are scented urea beads or the like.

From the foregoing, it is clear that the present invention provides a packaging structure for volatile substances, and particularly for room deoderizers, which is simple to activate, inexpensive, lightweight and unbreakable.

While presently preferred embodiments of the present invention have been illustrated and described, it is clear that the present invention may be otherwise variously embedded, within the scope of the following claims.

I claim:

1. A package comprising a pair of substantially similar pockets each having a volatile substance therein, said package comprising a pair of outer vapor-impermeable layers and a central vapor-permeable layer bonded along edge regions thereof to each of said vapor-impermeable layers to form said pair of pockets, said volatile material being positioned in each pocket between said central vapor-permeable layer and each said outer vapor-impermeable layer, said central vapor-permeable layer comprising a pair of bonded together vapor-permeable webs, the bond strength between said vapor-permeable webs being less than the bond strength between said central vapor-permeable layer and said outer vapor-impermeable layers.

2. The package of claim 1 wherein said outer vapor-impermeable webs include an unbonded edge or lip region.

3. The package of claim 1 wherein said outer vapor-impermeable layers are formed of a vapor-impermeable plastics resin film.

4. The package of claim 1 wherein said outer vapor-impermeable layers are formed of a plastics resin film-metallic foil-plastics resin film laminate.

5. The package of claim 4 wherein said laminate is a polyester film-aluminum foil-polyethylene film laminate.

6. The package of claim 1 wherein said central vapor-permeable layer is formed from a pair of bonded nonwoven rayon webs.

7. The package of claim 1 wherein said outer vapor-impermeable layers include an adhesive fastening means thereon.

8. The package of claim 7 wherein said adhesive fastening means comprises a tape.

9. The package of claim 1 wherein said volatile substance is an air deoderizer.

10. The package of claim 9 wherein said air deoderizer is formed from scented urea beads.

* * * * *